(12) United States Patent
Xian et al.

(10) Patent No.: US 10,520,509 B2
(45) Date of Patent: *Dec. 31, 2019

(54) FLUORESCENT PROBES FOR DETECTING HYDROGEN POLYSULFIDES

(71) Applicant: Washington State University, Pullman, WA (US)

(72) Inventors: Ming Xian, Pullman, WA (US); Wei Chen, Pullman, WA (US)

(73) Assignee: WASHINGTON STATE UNIVERSITY, Pullman, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/704,101

(22) Filed: Sep. 14, 2017

(65) Prior Publication Data

US 2018/0074068 A1   Mar. 15, 2018

Related U.S. Application Data

(60) Provisional application No. 62/394,625, filed on Sep. 14, 2016.

(51) Int. Cl.
| | |
|---|---|
| *C07D 493/10* | (2006.01) |
| *G01N 33/58* | (2006.01) |
| *C07D 323/00* | (2006.01) |
| *C07D 311/86* | (2006.01) |

(52) U.S. Cl.
CPC ......... *G01N 33/582* (2013.01); *C07D 311/86* (2013.01); *C07D 323/00* (2013.01); *C07D 493/10* (2013.01)

(58) Field of Classification Search
CPC ............................ G01N 33/582; C07D 493/10
See application file for complete search history.

(56) References Cited

U.S. PATENT DOCUMENTS 9,494,592 B2 * 11/2016 Xian .................... G01N 33/582

FOREIGN PATENT DOCUMENTS

FR          1000525       *  2/1952

OTHER PUBLICATIONS

Chen. Angewandte Chemie International Edition, 2015, 54(47), 13961-65, first online Sep. 18, 2015 (Year: 2015).*
Azirian. Dyes and Pigments, 2013, 99(2), 432-9 (Year: 2013).*
Chen. Chemical Science, 2013, 4, 2892-96 (Year: 2013).*
Wang. Faguang Xuebao, 2009, 30(4), 427-35 (Year: 2009).*
Mugaravel. Inorganic Chemistry, 2007, 46(26), 11048-62 (Year: 2007).*
Yin. Journal of Molecular Structure, 2004, 691(1-3), 33-37 (Year: 2004).*
Yan. Journal of Photochemistry and Photobiology, A; Chemistry, 1998, 116(3), 209-14 (Year: 1998).*
Wheelock. Journal of the American Chemical Society, 1958, 81, 1348-52 (Year: 1958).*

* cited by examiner

*Primary Examiner* — Noble E Jarrell
(74) *Attorney, Agent, or Firm* — W&C IP

(57) ABSTRACT

Reactive sulfur species have been recognized as an important regulator in redox biology, wherein the reactive sulfur species have been shown to be active in tumor suppressors, ion channels, and transcription factors. The disclosed invention is a novel composition of matter that allows for the detection of $H_2S$ and $H_2S_n$ species in living cells. These novel compositions represent significant progress in the field of chemical, $H_2S$ and $H_2S_n$ probes as they have both been successfully applied in the visualization sulfur species in living systems.

4 Claims, 5 Drawing Sheets

FLUORESCENT PROBES FOR DETECTING HYDROGEN POLYSULFIDES

CROSS-REFERENCE TO RELATED APPLICATION(S)

The present application claims under 35 U.S.C. § 119, the priority benefit of U.S. Provisional Application No. 62/394,625 filed Sep. 14, 2016. The disclosure of the foregoing application is incorporated herein by reference in its entirety.

FEDERAL FUNDING ACKNOWLEDGEMENT

This invention was made with government support under Grant/Contract No R01HL116571 awarded by the National Institutes of Health. The government has certain rights in the invention.

BACKGROUND OF THE INVENTION

Field of the Invention

This invention generally relates to fluorescent probes that take advantage of the reactivity of $H_2S$ and $H_2S_n$ species. These probes represent significant progress in the field, as they have both been successfully applied in the visualization of both exogenous and endogenous $H_2S$ and $H_2S_n$ in living cells.

Discussion of the Related Art

As a family, reactive sulfur species are sulfur-containing molecules that play a regulatory role in biological systems. Reactive sulfur species include biothiols and other s-modified protein cysteine adducts along with hydrogen sulfide and sulfane sulfur moieties such as persulfides, and polysulfides. Endogenous $H_2S_n$ may also be generated from $H_2S$ upon reacting with reactive oxygen species (ROS) such as $ClO^-$. Cystathionine γ-lyase (CSE) and cystathionine-β-synthase (CBS), the enzymes responsible for $H_2S$ biosynthesis, were found to also produce persulfides, which could further be converted to $H_2S_n$. $H_2S$ can also react with other sulfane sulfurs, such as $S_8$, to form $H_2S_n$.

The significance of $H_2S_n$ in redox biology has only recently been recognized, along with further research working to uncover additional biological mechanisms. As a general statement, the trend in the field currently suggests that $H_2S_n$ comprises signaling molecules that activate ion channels, transcription factors, and tumor suppressors with higher potency than $H_2S$. Additionally, physiological activities that have been attributed to being meditated by $H_2S$ have also been shown to be meditated by $H_2S_n$. With one such example being S-sulfhydration, wherein a posttranslational modification is the result of $H_2S$ activity. But, it was also observed that $H_2S_n$ are more effective than $H_2S$ in S-sulfhydration. As such a greater understanding of the mechanisms of action governing sulfur species has become an active area of research.

Despite the increased interest in this area of research, there still remain many fundamental questions regarding the production and the mechanism of action of reactive sulfur species. Traditional methods for detecting sulfur species in a sample resulted in suspending a sample in a solution and measuring the UV/Vis absorption bands at 290-300 nm and 370 nm to determine the presence of $H_2S_n$. However, this method has low sensitivity and is not applicable for biological detections. Fluorescence assays could be useful because of their high sensitivity and spatial/temporal resolution capability. Initial attempts at developing similar fluorescent probes employed a 2-fluoro-5-nitrobenzoic ester template to trap $H_2S_n$ and allowed for an intramolecular cyclization to release a fluorophore. Other attempts adopted similar chemical templates, but also introduced new drawbacks.

SUMMARY OF THE INVENTION

The present invention provides fluorescent probes and methods for their use in detecting $H_2S$ and $H_2S_n$ species. This novel innovation allows for the detection and characterization of $H_2S$ and $H_2S_n$ species in a plurality of environments but notably allows for the detection of these species in living systems.

In one aspect of the disclosed invention includes a compound generally referred to as a reaction based fluorescent probe (such as PSP), of Formula I:

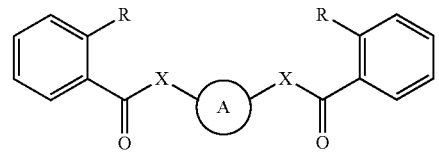

or an acceptable salt thereof, wherein, R=—SH, —SeH, —OH, —$SO_2$H, —CN, —$CH_2$CN, —S(CO)$R_1$, wherein $R_1$ is selected from the group consisting of substituted alkyl, alkyl, substituted aryl and aryl, X is a heteroatom such as oxygen, or in some embodiments it can also be a alkyl or amino group and ring A is a heterocyclic fluorophore that can be either a monocyclic hertercycle or a bicyclic hertercycle. Wherein the monocyclic heterocycle is a 1, 2, or 3 membered ring containing at least on heteroatom wherein the ring is saturated or unsaturated with some examples being of the chemical formula:

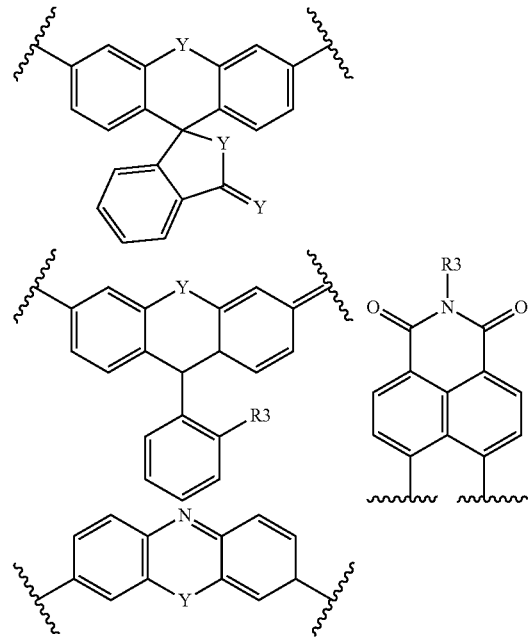

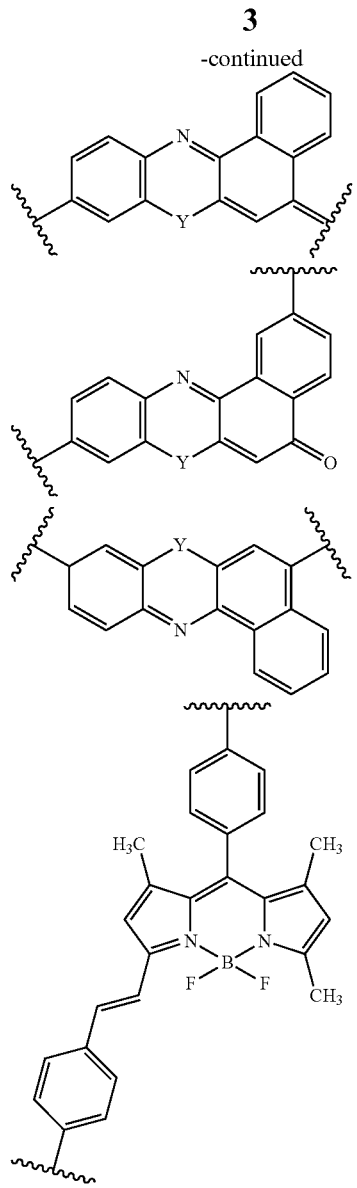

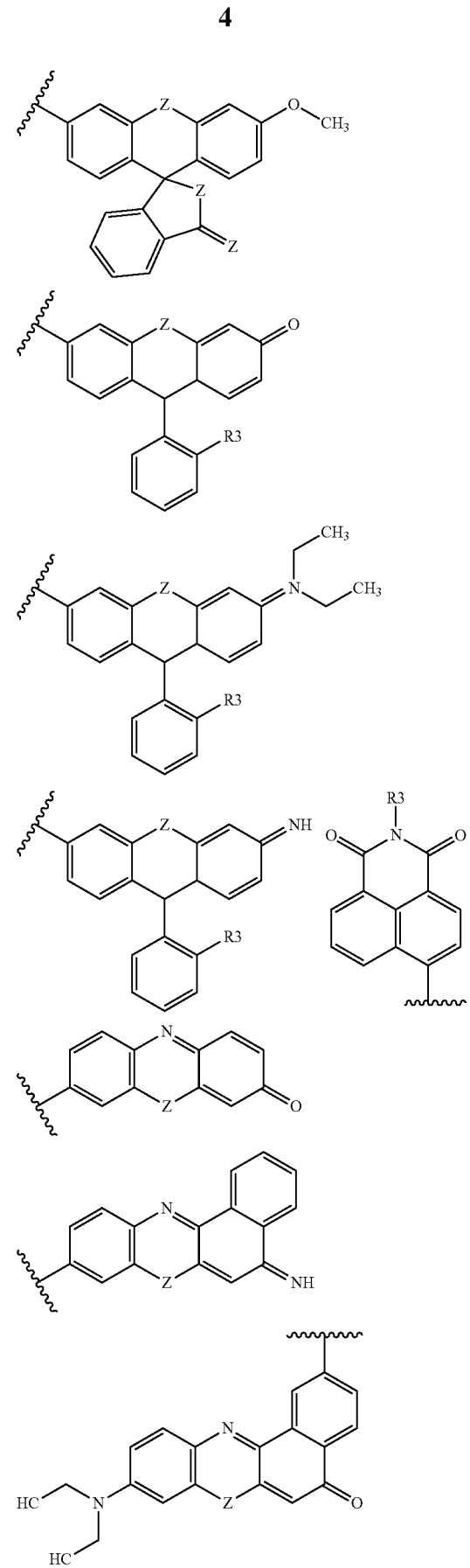

wherein Y is selected from the group containing C, O, N or Si and $R_3$ is selected from the group COOH, $(CH_2)_nCH_3$ (n≥0), $(CH_2)_nCOOH$ (n≥1), $(CH_2)_nCOOCH_3$ (n≥1), or $(CH_2)_nCOOC_2H_5$ (n≥1), $(CH_2)_nCONH(CH_2)_nPPh_3$ (n≥1), or $CH_3$.

In another aspect, the disclosed invention includes a compound generally referred to having the structure:

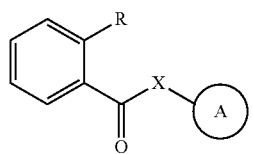

or an acceptable salt thereof, wherein, R=—SH, —SeH, —OH, —SO$_2$H, —CN, —CH$_2$CN, —S(CO)R$_1$, wherein R$_1$ is selected from the group consisting of substituted alkyl, alkyl, substituted aryl and aryl, X is a heteroatom such as oxygen, or in some embodiments it can also be a alkyl or amino group and ring A is a heterocyclic fluorophore with some examples being of the chemical formula:

-continued
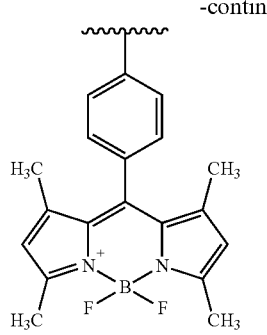
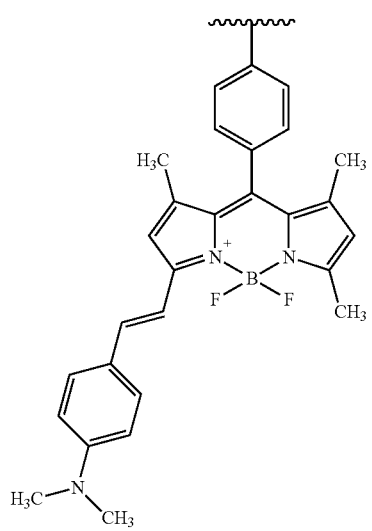
-continued
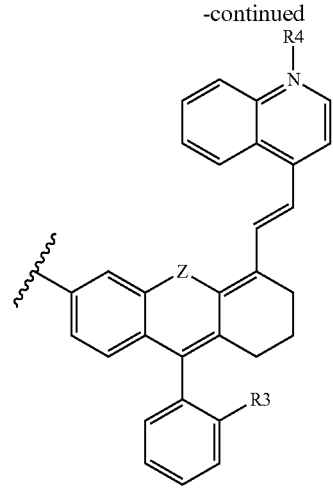
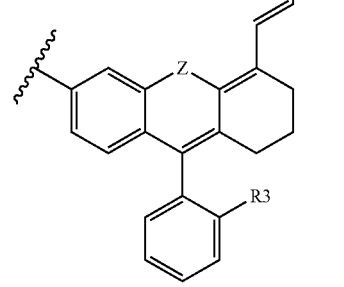
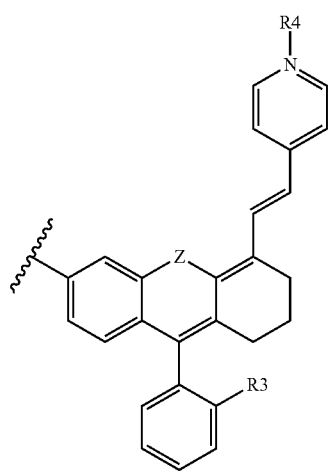
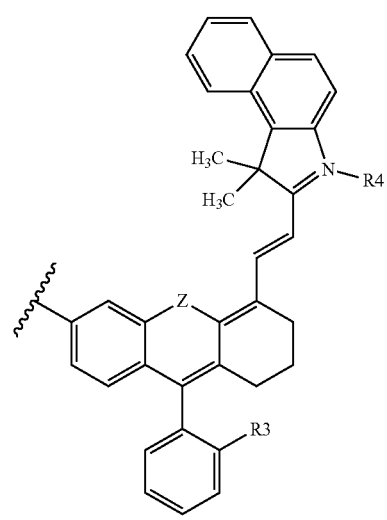

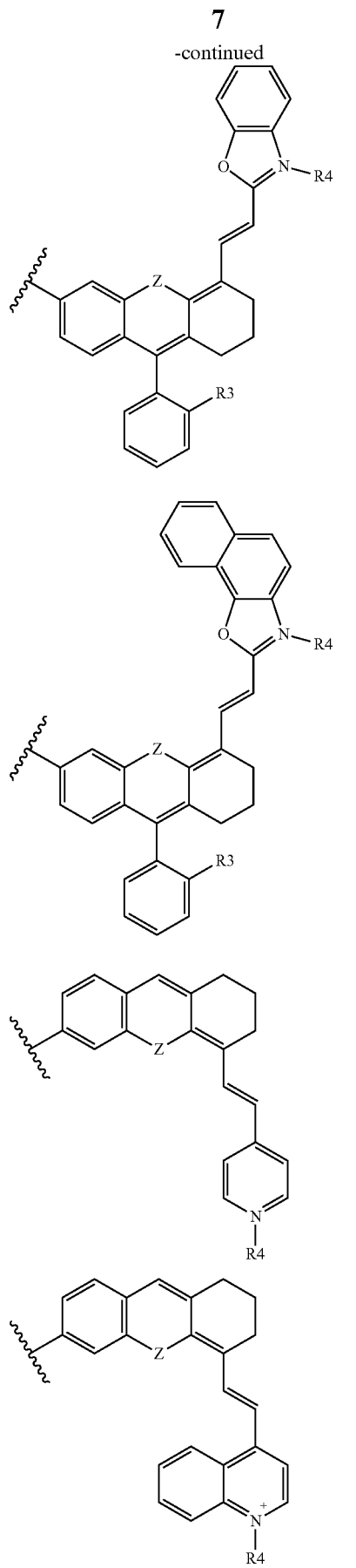
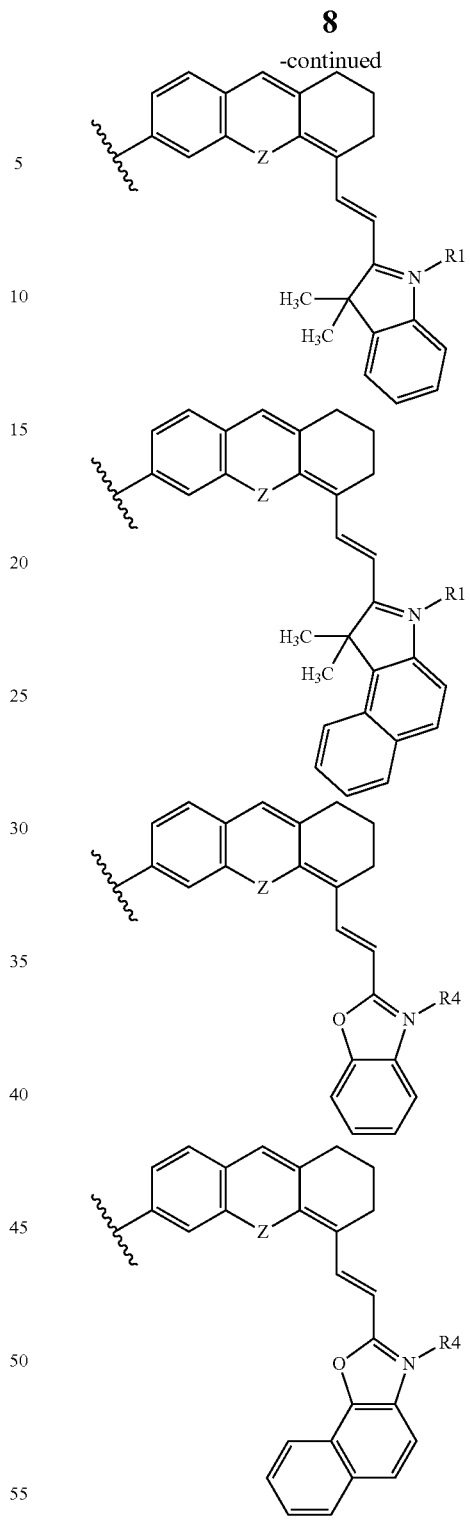

Wherein Z is selected from the group containing C, O, N or Si and $R_3$ is selected from the group COOH, $(CH_2)_nCH_3$ (n≥0), $(CH_2)_nCOOH$ (n≥1), $(CH_2)_nCOOCH_3$ (n≥1), or $(CH_2)_nCOOC_2H_5$ (n≥1), $(CH_2)_nCONH(CH_2)_nPPh_3$ (n≥1), or $CH_3$ and $R_4$ is selected from the group $(CH_2)_nCH_3$ (n≥0) and Q is selected form the O or S.

In another aspect, the embodiments herein includes a compound generally referred to as a PSP probe having the structure:

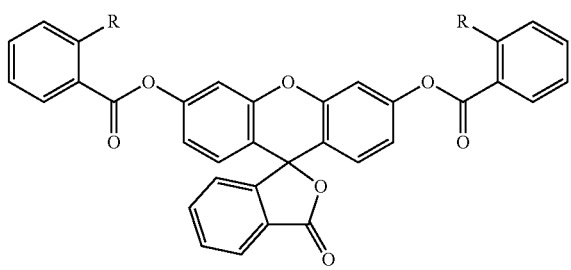

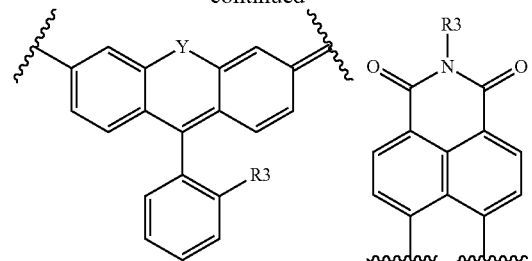

Or an acceptable salt thereof, wherein, R=—SH, —SeH, —OH, —SO$_2$H, —CN, —CH$_2$CN, —S(CO)R$_1$, wherein R$_1$ is selected from the group consisting of substituted alkyl, alkyl, substituted aryl and aryl.

In another aspect, the invention provides a dual-detection fluorescent-probe generally referred to as dual detection fluorescent (DDP) probe, having Formula II:

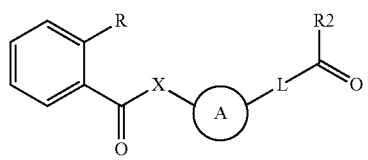

Or any acceptable salt thereof, wherein X is a heteroatom such as oxygen, or in some embodiments it can also be a alkyl or amino, R=—SH, —SeH, —OH, —SO$_2$H, —CN, —CH$_2$CN, —S(CO)R$_1$; R$_1$ is selected from the group consisting of substituted alky, alky, substituted aryl and aryl; L is a linker selected from the group consisting of piperazine cyclohexane-1,4-diamine/4-aminopiperidine/1-(piperidin-4-yl)piperazine/[1,4'-bipiperidin]-4-amine; R2=alkyl, substituted alkyl, —CH$_2$R$_3$, —O-substituted alkyl; and R3 is a compound with the chemical formula:

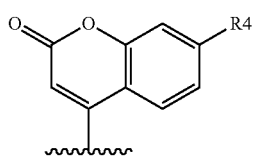

wherein, R$_4$ is azide, nitro, nitroso, hydroxyamine, and any other reducible groups; and ring A is a fluorophore selected from the compounds with chemical formula:

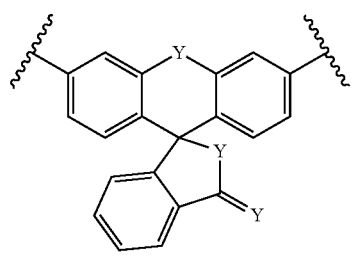

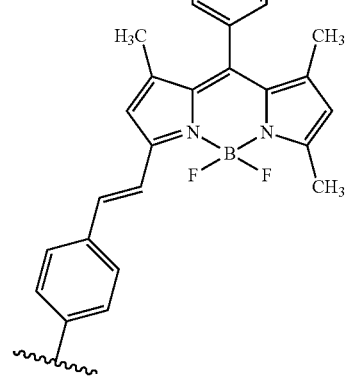

wherein Y is selected from the group containing C, O, N or Si and R$_3$ is selected from the group COOH, (CH$_2$)$_n$CH$_3$ (n≥0), (CH$_2$)$_n$COOH (n≥1), (CH$_2$)$_n$COOCH$_3$ (n≥1), or (CH$_2$)$_n$COOC$_2$H$_5$ (n≥1), (CH$_2$)$_n$CONH(CH$_2$)$_n$PPh$_3$ (n≥1), or CH$_3$ and R2 is a compound with a chemical formula:

In another aspect, the invention provides a dual-detection fluorescent-probe having the following structure:

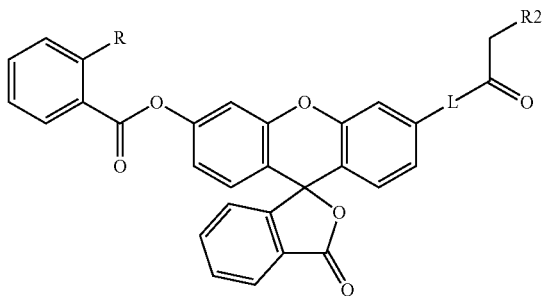

Or an acceptable salt thereof, wherein, R=—SH, —SeH, —OH, —SO$_2$H, —CN, —CH$_2$CN, —S(CO)R$_1$, wherein R$_1$ is selected from the group consisting of substituted alkyl, alkyl, substituted aryl and aryl; L is a linked selected from the group consisting of piperazine, cyclohexane-1,4-diamine/4-aminopiperidine/1-(piperidin-4-yl)piperazine/[1,4'-bipiperidin]-4-amine and wherein R2 is a compound having a structure

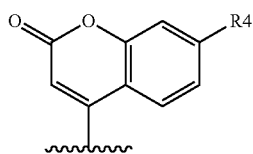

wherein, R$_4$ is an azide, nitro, nitroso, hydroxylamine, and any other reducible group.

Accordingly, such probes and methods of use can be utilized to either detect H$_2$S, H$_2$S$_n$ or other reactive sulfur species in a living system, such as, for example, aqueous media, cells, and tissues. Beneficially, the probes can also be used to differentiate between H$_2$S and H$_2$S$_n$ in a living system, such as the aforementioned aqueous media and cells.

The foregoing and other objects, features, and advantages of the present disclosure will become more apparent from the following detailed description, which proceeds with reference to the accompanying figures.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Fluorescence images of exogenous H$_2$S$_n$ in HeLa (a-c), RAW264.7 (d-f), and Vero (g-i) cells.

Figure 6:
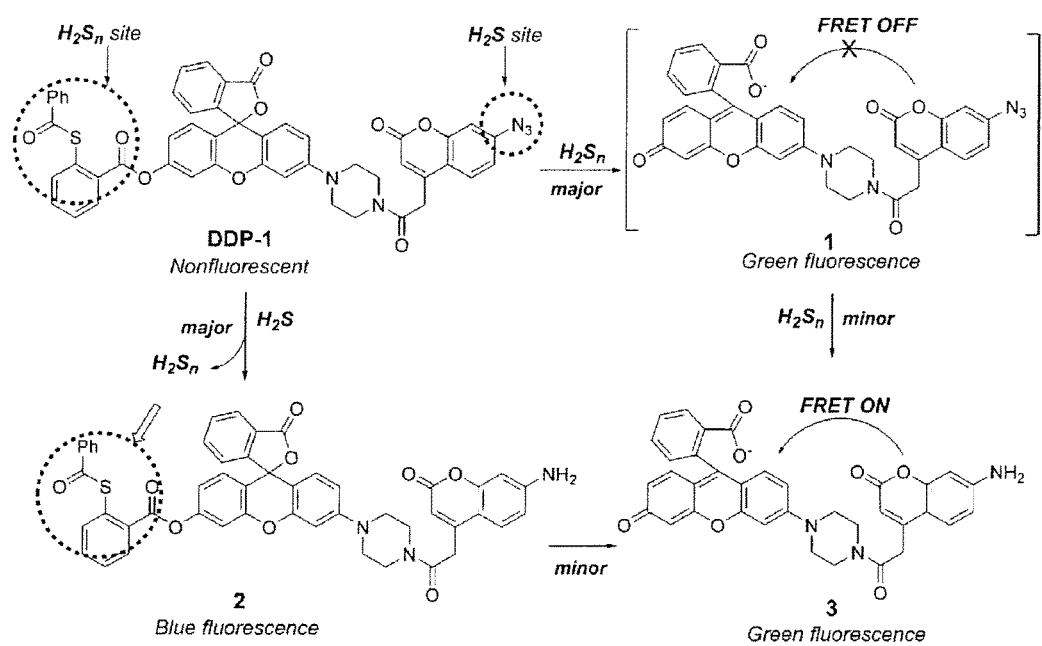

FIG. 6 shows the reaction scheme and design of the DDP-1 probes.

Figure 7:
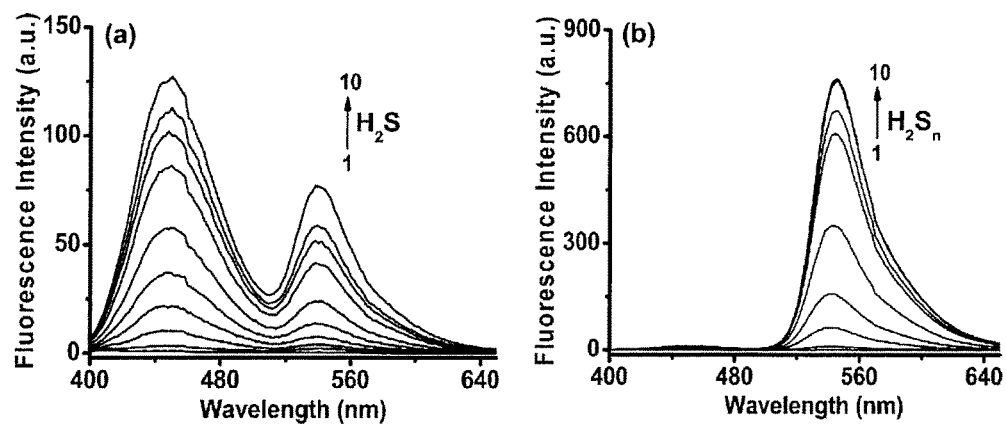

FIG. 7 shows Fluorescence spectra of DDP-1 (10 μM) under various concentrations of H$_2$S and H$_2$S$_n$.

Figure 8:
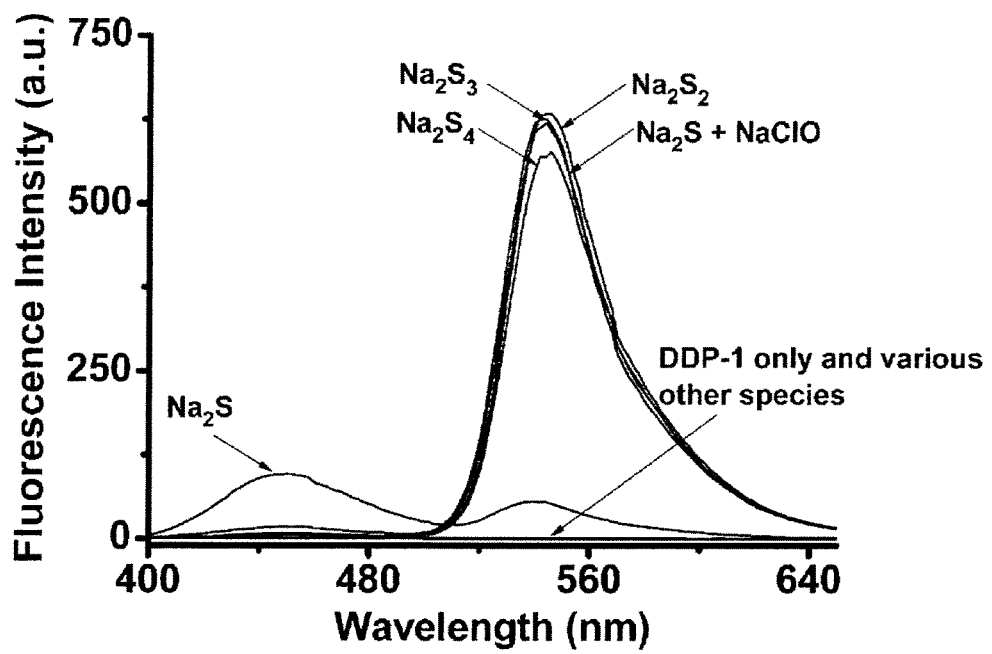

FIG. 8 shows Fluorescence emission spectra ($\lambda_{ex}$=360 nm) of DDP-1 (10 μM) in the presence of various reactive species.

Figure 9:
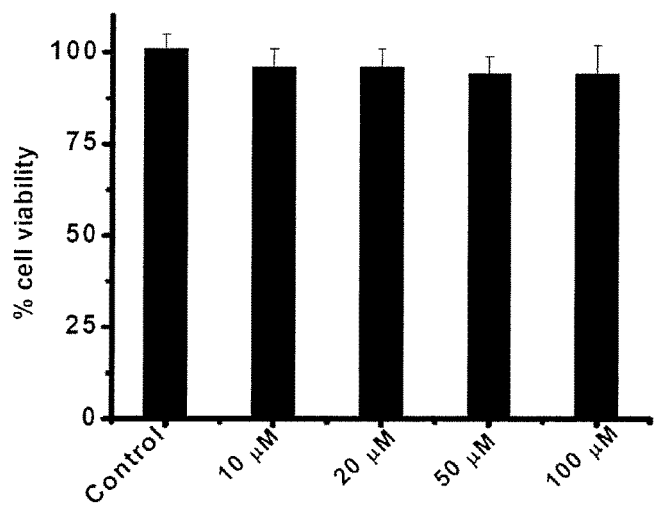
Figure 10:
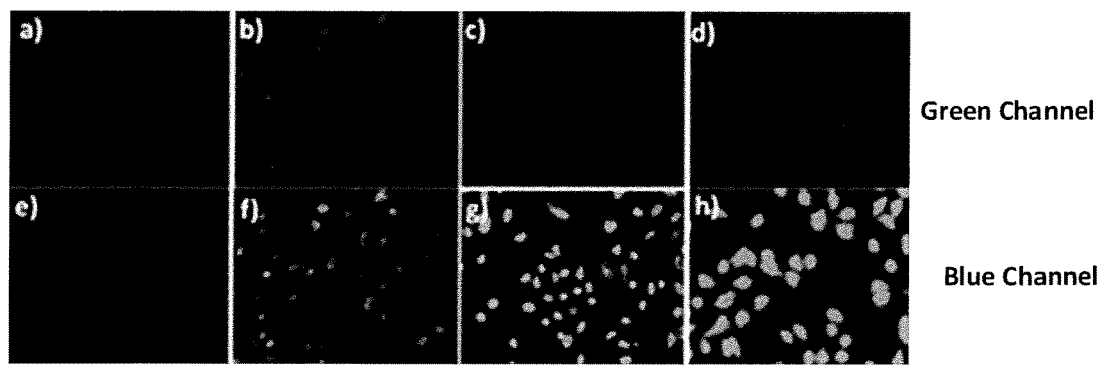

FIG. 9 shows the cytotoxicity studies of DDP-1 (10 μM; 20 μM; 50 μM, 100 μM) for HeLa Cells FIG. 10 shows HeLa cells incubated with DDP-1 (20 μM) for 30 min, then washed, and subjected to different treatments. a, e) Controls (no added Na$_2$S, NaClO, or Na$_2$S$_2$); b, f) Na$_2$S (100 μM); c, g) the mixture of Na$_2$S (100 μM) and NaClO (50 μM); d, h) Na$_2$S$_2$ (50 μM). a-d) Fluorescence image of HeLa cells at the blue channel; e-h) fluorescence image of the corresponding image (a-d) from green channel.

DETAILED DESCRIPTION

The following are definitions of terms that may be used in the present specification. The initial definition provided for a group or term herein applies to that group or term throughout the present specification individually or as part of another group, unless otherwise indicated.

The term "living system" refers to a cell that is in vitro, ex vivo or in vivo. In some embodiments, an ex vivo cell can be a part of a tissue sample excised from an organism such as a mammal. In some embodiments, an in vitro cell can be a cell in a cell culture. In some embodiments, an in vivo cell is a cell living in an organism such as a mammal.

The term "heterocyclyl" or "heterocyclic" refers to a monocyclic hertercycle or a bicyclic hertercycle. The monocyclic heterocycle is a 3, 4, 5, 6, or 7 membered ring containing at least on heteroatom independently selected from the group consisting of O, N, and S wherein the ring is saturated or unsaturated. The monocyclic heterocycles can be connected to a parent molecule moiety through any carbon atom or any oxygen or nitrogen atom attached to or incorporated within the monocyclic heterocycle. Bicyclic heterocycles are monocyclic heterocycle fused to either a phenyl, a monocyclic cycloalky, a monocyclic cycloalkenyl, a monocyclic heterocycle, or a monocyclic heteroaryl. The bicyclic heterocycle is connected to the parent molecule moiety through any carbon atom or any oxygen or nitrogen atom attached to or incorporated within the bicyclic ring system. Heterocyclyl groups are optionally substituted with one or two groups which are independently selected from the group consisting of O, N, and S.

The term "saturated" refers to a chemical structure that does not contain any multiple carbon-carbon bonds. For example, a saturated cycloalkyl group as defined herein includes cyclohexyl, cyclopropyl and the like.

The term "unsaturated" refers to a chemical structure that contains at least one multiple carbon-carbon bond, but is not aromatic. For example, a unsaturated cycloalkyl group as defined herein includes cyclohexenyl, cyclopentenyl, cyclohexadienyl, and the like.

The term "nucleophile", by itself means a chemical species that donates an electron-pair to an electrophile to form a chemical bond in a reaction. Because nucleophiles donate electrons, they are by definition Lewis bases. All molecules or ions with a free pair of electrons can act as nucleophiles.

The term "fluorophore", by itself means chemical compounds containing at least one aromatic group, or planar or cyclic molecules with several π bonds and can re-emit light upon light excitation.

The term "acceptable salt" means a salt from of a compound with alkali metals such as sodium, potassium and lithium, with alkaline earth metals such as calcium and magnesium, with organic bases such as dicyclohexylamine, tributylamine, pyridine and amino acids such as arginine, lysine and the like. Compounds may also form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

The term "alkyl" refers to straight or branched chain hydrocarbon, which may be fully saturated, mono-saturated or polyunsaturated containing from 1-10 carbon atoms, unless otherwise specified. For convenience, the term alkyl may refer to divalent (i.e., alkalyne) configurations. Representable examples of alkyl include, but are not limited to, methyl, ethyl, n-propyl, iso-propyl, n-butyl, tert-butyl, isobutyl, sec-butyl, n-pentyl, isopentyl, neopentyl, cyclohexyl, methyl, cyclopropylmethyl, as well as homologs and isomers thereof.

Typically, an alkyl (or alkylene) group will have from 1 to 30 carbon atoms. That is, in some embodiments, alkyl refers to an alkyl having a number of carbons such as, but not limited to, C1 to $C_{30}$ or greater and any combination thereof.

The term "substituted" refers to hydrocarbon compound (e.g. an alkyl, alkenyl, alkynyl, ring, etc. structure as described herein) in which an H bonded to a C is replaced or substituted by a different atom or groups of atoms e.g. a saturated 6-membered straight chain in which the 2 terminal C atoms are bonded to three H atoms, three of the four internal C atoms are bonded to 2H atoms, and one of the internal C atoms is bonded to H and also to a different atom or group of atoms (e.g. OH). In this case, the hydrocarbon chain is "substituted" by (with) OH.

The term "substituted alkyl" refers to an alkyl group substituted by, for example, one to four substituents, such as, ketone, halo, hydroxy, alkoxy, oxo, alkanoyl, aryloxy, alkanoyloxy, amino, alkylamino, substituted alkylamino, cycloalkylamino, substituted cycloalkylamino, acylamino, substituted arylamino, aralkylamino, substituted aralkyamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like.

The term "aryl" refers to monocyclic or bicyclic aromatic hydrocarbon groups having 6 or more carbon atoms in the ring portion, such as phenyl, naphthyl, biphenyl and diphenyl groups, each of which may be substituted. In some embodiments, aryl can be a 3, 4, 5, 6, 7 or 8 membered ring that is fused to one or two other 3, 4, 5, 6, 7 or 8 membered rings.

The term "substituted aryl" refers to an aryl group substituted by, for example, one to four substituents such as alkyl, substituted alkyl, alkenyl, substituted alkenyl, alkynyl, substituted alkynyl, aryl, substituted aryl, aralkyl, halo, trifluoromethoxy, trifluoromethyl, hydroxy, alkoxy, alkanoyl, alkanoyloxy, aryloxy, aralkyloxy, amino, alkylamino, arylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or aralkyl.

In some embodiments, the definition of terms used herein is according to International Union of Pure and Applied Chemistry (IUPAC) naming standards. Additionally, it will be understood that any list of such candidates or alternatives are merely illustrative, and not limiting, unless implicitly or explicitly understood or stated otherwise.

As used in this specification and the appended claims, the singular forms "a", "an" and "the" include plural referents unless the content clearly dictates otherwise. In addition, unless otherwise indicated, numbers expressing quantities of ingredients, constituents, reaction conditions and so forth used in the specification and claims are to be understood as being modified by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

General Description

The general usefulness of the disclosed invention lies in the selective detection of $H_2S$ and $H_2S_n$ species either together or individually in living cells. The disclosed probes rely on the reactivity of sulfur species in said living cells. $H_2S_n$ are reactive and labile, additionally they often exist as a thiosulfoxide tautomer. Such properties provide very highly reactive intermediates from which the sulfur atom can be readily reacted with nucleophilic groups. This reactivity allows the disclosed probes to take advantage of specific chemistry and as a result be selective for specific sulfur species.

One of the benefits of the several embodiments disclosed herein is that they do not interfere with the other biologically relevant sulfur species such as cysteine, glutathione, thiosulfate, sulfite, and sulfate. As such, aspects of the invention provide for either a singular or dual reactive fluorescent probe for sensing and imaging $H_2S_n$ or $H_2S$ moieties to include, a nucleophile, a fluorophore, and a modified fluorophore attached via a linker. Using various embodiments of the invention, the concentration of both hydrogen sulfide and/or hydrogen polysulfides can be determined by their fluorescence signal.

More notably, the disclosed methods don't require the destruction of living tissues, thus allowing for the fluorescence and detection of $H_2S_n$ or $H_2S$ to occur in living cells and tissues. Additionally, the disclosed probes are easy to use along with being safe and relatively low in toxicity. The above mentioned qualities allow for the disclosed invention to have biochemical and biomedical research applications that include clinical and drug development assays.

The compounds disclosed herein can thus be used in real time imaging of $H_2S_n$ or $H_2S$ in living cells. Along with being utilized in various biomedical applications, such compounds enable the study of, for example, the role of endogenously produced $H_2S_n$ or $H_2S$ in living cellular models. Additionally, the disclosed probes can be used in clinical and drug-development assays by providing rapid method to assess the level of $H_2S_n$ or $H_2S$ within a given model.

Specific Description

Figure 1:
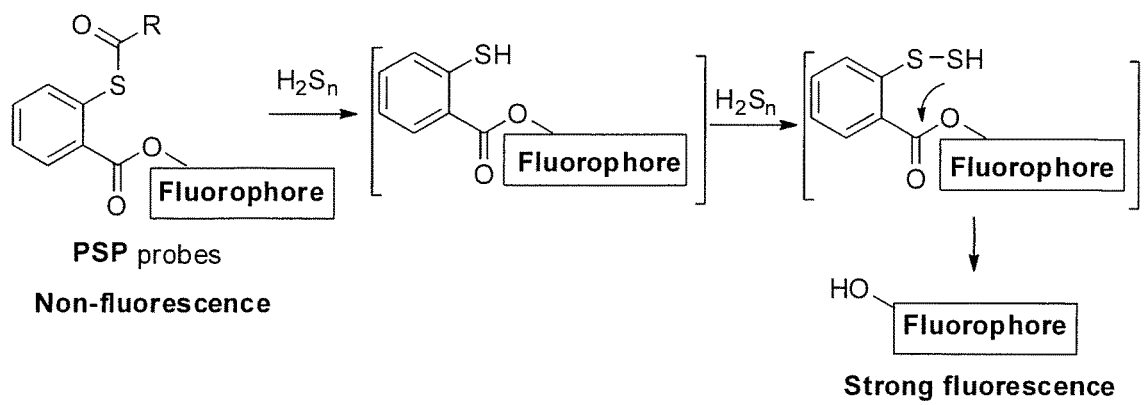
FIG. 1 shows the reaction scheme and design of an exemplary example of a PSP fluorescent probes.
Figure 2:
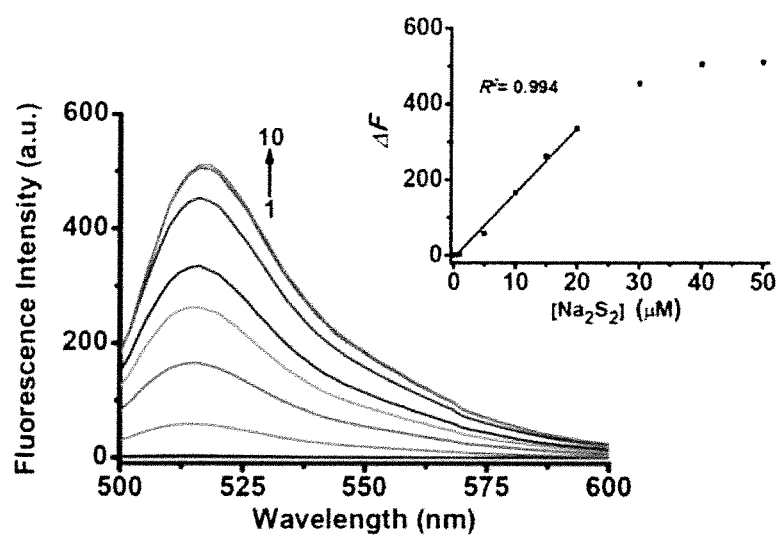
FIG. 2 shows the fluorescence emission spectra of PSP-3 (10 μM) with varied concentrations of Na$_2$S$_2$ (0, 0.25, 1, 5, 10, 15, 20, 30, 40, 50 μM for curves 1-10, respectively).
Figure 3:
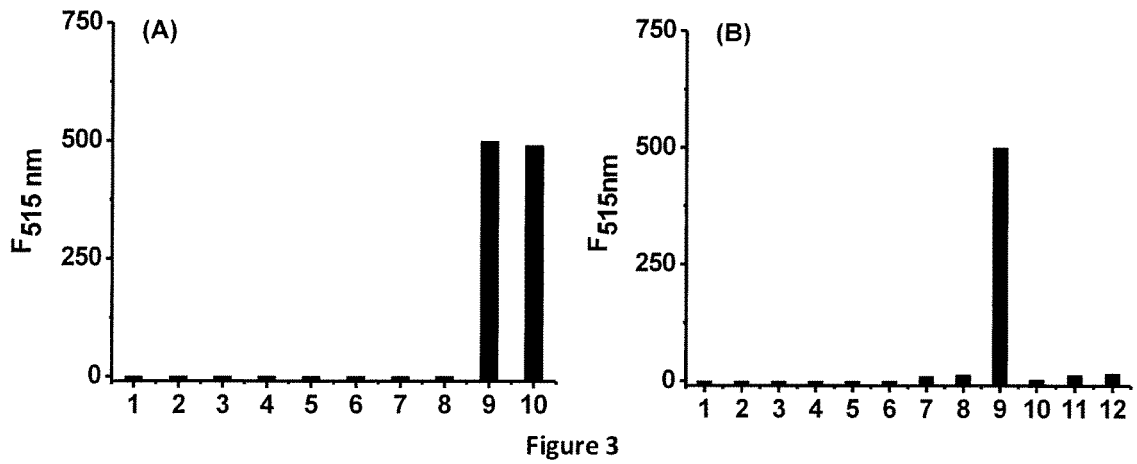
FIG. 3 shows the selectivity data of PSP probes.

The concept underpinning of the PSP probes is illustrated in FIG. 1, wherein thioesters can further react with an $H_2S_n$ species to activate the compound and allow for fluorescence. To demonstrate the efficiency of PSP probes in detecting $H_2S_n$ concentration, varying concentrations of $Na_2S_2$ were tested with select fluorescence probes as shown by FIG. 2. The fluorescence intensity increased linearly with the concentration of $Na_2S_2$ changed up to 25 μM, and, thereafter reached a steady state. It should be noted that the reaction that yields fluorescence is slower and tends to yield less fluorescence when the $H_2S_n$ concentration is lower. But, at higher loads the fluorescence of the compound can be easily detected. As seen in FIG. 3, the fluorescent intensity of 10 μM PSP-3 in the presence of various sulfur species: (1) probe alone; (2) 100 μM Hcy; (3) 100 μM GSSG; (4) 200 μM $Na_2S$; (5) 100 μM $Na_2S_2O_3$; (6) 100 μM $Na_2SO_3$; (7) 100 μM $Na_2SO_4$; (8) 100 μM $CH_3SSSCH_3$; (9) 50 μM $Na_2S_2$; (10) 50 μM $Na_2S_4$. The graph labeled B shows the Fluorescence intensity of PSP-3 (10 μM) in the presence of selected reactive sulfur species with or without $H_2S$. The data shows the superior selectivity of the PSP probes while still demonstrating that there is little to no reactivity with biothiols or other sulfur species under physiological concentrations.

In one embodiment of the disclosed invention, the reactive groups have been designed to only react with $H_2S_n$ and not react with other sulfur species, especially biothiols. From a chemistry stand point, $H_2S_n$ derivatives are quite different from thiols or $H_2S$. The estimated pKa values of $H_2S_n$ are in the range of 3 to 5. By comparison the pKa value for $H_2S$ and biothiols are in the range of 7 to 9.2. As such, at a physiological pH, $H_2S_n$ are expected to be anionic species and as such, will function as more reactive nucleophiles than biothiols and $H_2S$ as a result of the alpha effect.

Figure 4:
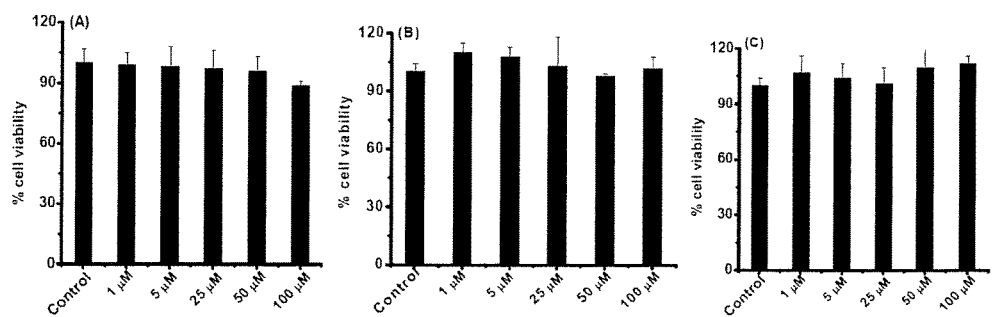
FIG. 4 shows the cytotoxicity data of PSP-3 (1 μM; 5 μM; 25 μM, 50 μM, 100 μM) for: (A) HeLa Cells; (B) RAW264.7 cells; (C) Vero Cells.
Figure 5:
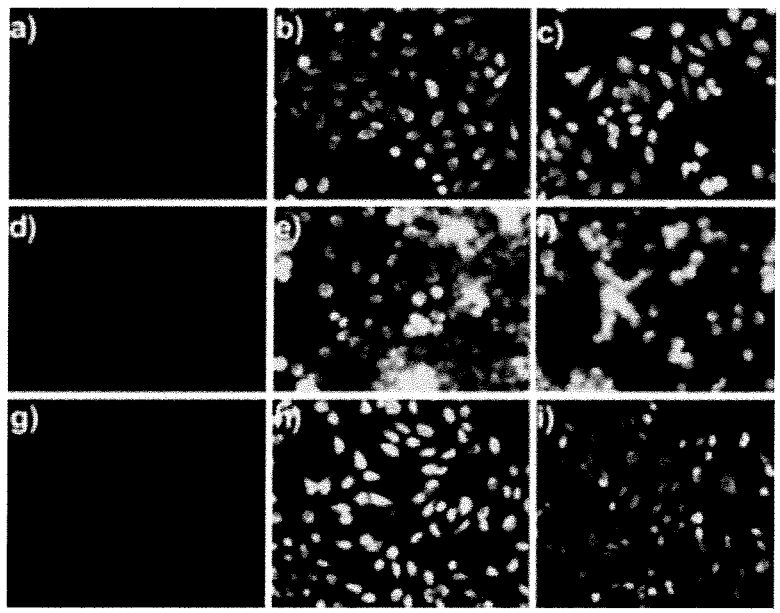
FIG. 5 shows fluorescence imaging photos of PSP-3 in the presence of H$_2$S$_n$.

In another embodiment the PSP probes can have been designed to visuals exogenous sulfur species in a living system. As seen in FIG. 4, (a) HeLa, (b) RAW264.7, and (c) Vero cells were incubated in the presence of a PSP at varying concentrations to demonstrate that the compounds don't induce cytotoxicity in the treated cells. Additionally, the selectivity of the probes can be seen in FIG. 5. The figure shows the probe in the presence of $H_2S_n$, the image of exogenous H2Sn in HeLa (a-c), RAW264.7 (d-f), and Vero (g-l) cells. The selected cells where incubated in the probe (5 μM) for 25 min, then washed and subjected to different treatments that included treating the cells with 30 μM of $Na_2S_2$ (b,e,h) and cells treated with 30 μM of $Na_2S_4$ (c,f,i) along with the controls with nothing added (a,d,g). Other biologically relevant sulfur species that can be detected, including cysteine, glutathione, homocysteine, oxidized glutathione, $H_2S$, thiosulfate, sulfite and sulfate, show little to no significant fluorescence. These results demonstrate good selectivity of PSP probe for the desired target.

In another embodiment of the disclosed invention, the fluorescence probe such as DDP was designed to react and distinguish between $H_2S_n$ and $H_2S$. In the design of such a probe, four factors were considered. The first being the selection of a fluorophore, coumarin and rhodol were selected as two fluorophores due to their excellent solubility, high quantum yields, and well-separated maximum emission wavelengths (ca. 445 nm for coumarin and ca. 542 nm for rhodol). As such, dual-color imaging of $H_2S$ and $H_2S_n$ from different emission channels was possible. The second factor is the selection of a linker. To that end, a rigid piperazine linker was used to bridge the two fluorophores and provide an advantage for Förster resonance energy transfer (FRET) in the coumarin-rhodol scaffold, which prevents the π-π stacking between dyes. The third factor is the azidation of coumarin and phenyl 2-(benzoylthio)benzoate-protected rhodol to effectively quench the fluorescence of the probe via the intramolecular charge transfer (ICT) effect and the intramolecular spirocyclization, respectively. The fourth and final factor, is the azide and phenyl 2-(benzoylthio)benzoate moieties provide selective reaction sites for $H_2S$ and $H_2S_n$.

The fluorescence turn-on mechanism of DDP-1 is shown in FIG. 6. When the probe is treated with $H_2S_n$, phenyl 2-(benzoylthio)benzoate preferably reacted to release the fluorescence of rhodol. Even if the azide group is partially reduced by $H_2S_n$ to form a small amount of 3, it should not affect the fluorescence emission channel due to FRET between the two fluorophores. Overall the reaction with $H_2S_n$ should only produce green fluorescence of rhodol. In contrast, the reaction between DDP-1 and $H_2S$ is more complicated. Previous results have demonstrated that $H_2S$ cannot turn on phenyl 2-(benzoylthio)benzoate-based fluorophore. Therefore, $H_2S$ would preferably react with the azide moiety to produce 2 and release blue fluorescence of coumarin. It should be noted that recent studies demonstrated that the reaction of $H_2S$ with azides led to the formation of $H_2S_n$. Therefore, 3 would also be formed in this process, which should exhibit green fluorescence of rhodol because of FRET. However, less than 0.5 equivalent of $H_2S_n$ are generated from the reaction of 1 equivalent of $H_2S$ and the azide. Moreover, the reaction with phenyl 2-(benzoylthio)benzoate consumes at least 2 equivalent of $H_2S_n$. Therefore, only a small amount of 3 would be produced during this process. Overall the reaction between DDP-1 and $H_2S$ should produce the emission signals of both coumarin (major) and rhodol (minor).

The sensitivity of the DDP $H_2S$ and $H_2S_n$ using varied concentrations of $Na_2S$ or $Na_2S_2$ (0 to 150 μm). FIG. 7 shows the increase in fluorescence intensity ($\lambda_{ex}$=360 nm) with the gradual increase of $Na_2S$ or $Na_2S_2$ concentrations was observed. For $H_2S$, the fluorescence intensity at 452 nm increased linearly with $Na_2S$ concentration from 0 to 20 μm. The fluorescence intensity at 542 nm increased linearly with $Na_2S$ in the concentration range of 0 to 40 μm. The detection limits (S/N=3) were 100 nm and 150 nm for $H_2S$, corresponding emission at 452 and 542 nm. The fluorescence intensity at 542 nm increased linearly with $Na_2S_2$ concentrations from 0 to 20 μm. The detection limit was calculated to be 24 nm. As a result, the DDP probes displayed much higher sensitivity to $H_2S_n$ than $H_2S$, and that pH has an effect on the reactivity. With probe operating more effectively at neutral to basic pH's.

Given the dual reactive nature of the DDP probe there was a need for establish a meaningful responses when $H_2S$ and H2S$_n$ co-exist. To this end, fluorescence changes of varying Na$_2$S$_2$/Na$_2$S mixture solutions where examined, while the total sulfur concentration was fixed in samples (200 μm). As H$_2$S is a much more stable species than H$_2$S$_n$ and the concentration of H$_2$S is likely to be higher than H$_2$S$_n$ in biological systems, we varied [H$_2$S$_2$]/[H$_2$S] ratios from 0 to 1. The fluorescence signals of these solutions were measured by the probe. As shown in FIG. 8 the increases of [H$_2$S$_2$]/[H$_2$S] ratios, the emission at 452 nm decreased with a concurrent increase at 542 nm. The $F_{542\ nm}/F_{452\ nm}$ ratios increased linearly with [H$_2$S$_2$]/[H$_2$S] ratios in the range of 0 to 0.176. Showing that the DDP probe could be used for the ratiometric detection of relative H$_2$S$_n$ and H$_2$S concentrations when they coexist.

In another embodiment the DDP probes has been designed to visuals exogenous sulfur species in a living system. As seen in FIG. 9, HeLa cells were incubated in the presence of a DDP probe at varying concentrations to demonstrate that the compounds don't induce cytotoxicity in the treated cells. Additionally, the selectivity of the probes can be seen in FIG. 10. The figure shows the probe in the presence of H$_2$S$_n$ and H$_2$S, in HeLa cells. The probe (20 μm) was applied to the cells for 30 minutes, after which the extracellular probe was washed off and only a weak fluorescence was observed. When cells were treated with Na$_2$S (100 μm), an apparent fluorescence enhancement was detected in the blue and green channel. When cells were treated with Na$_2$S$_2$ or in situ generated H$_2$S$_n$, the fluorescence signals in the blue channel decreased with a coinstantaneous increase in the green channel. These results demonstrate that DDP probes where could be used for the detection of H$_2$S and H$_2$S$_n$ from distinct emission channels in cells. Additionally, the cell viability assay implied that DDP has low cytotoxicity and good biocompatibility Both the PSP and DDP-1 probes are designed with a fluorophore attached via a linker or a substituted aryl a group leading to a fluorophore or modified fluorophore group. The electrophile is positioned suitably for cyclization reaction, to release the fluorophore and produce either a self-quenching reaction with via a reduction leading to a blue florescence via a reduction of the reactive group on the fluorophores. An alternative reaction can occur at the sulfur leading a systematic collapse and release of the fluorophores from the base structure.

The mechanisms of action of these probes have been fine tuned to detect the present of H$_2$S$_n$ or H$_2$S. When the probe is treated with a source of H$_2$S$_n$. the reaction occurs that will release a fluorophore.

The fluorescence properties of the probes disclosed herein were tested in aqueous PBS buffer solution (pH 7.4). The thioester group of PSP probes is used to trap H$_2$S$_n$ in the desired target. The resulting intermediate adducts undergo a fast intermolecular cyclization to release strong fluorescent molecules, as well as benzodithiolone.

EXAMPLES

Materials and Methods

All solvents were reagent grade. Reactions were magnetically stirred and monitored by thin layer chromatography (TLC) with 0.25 mm pre-coated silica gel plates. Flash chromatography was performed with silica gel 60 (particle size 0.040-0.062 mm). Yields refer to chromatographically and spectroscopically pure compounds, unless otherwise stated. Proton and carbon-13 NMR spectra were recorded on a 300 MHz spectrometer.

Chemical Synthesis

Chemical shifts are reported relative to dimethyl sulfoxide (δ2.50) for 1H NMR and dimethyl sulfoxide (δ39.51) for 13 C NMR. Absorption spectra were recorded on a 300 UV/VIS spectrophotomer using a 1 cm quartz cell. Fluorescence excitation and emission spectra were measured on Cary Eclipse fluorescence spectrophotometer.

Synthesis of Probe Precursor

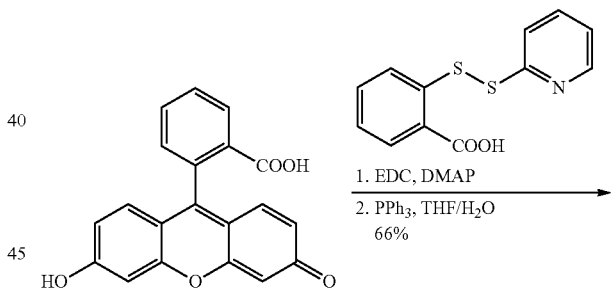

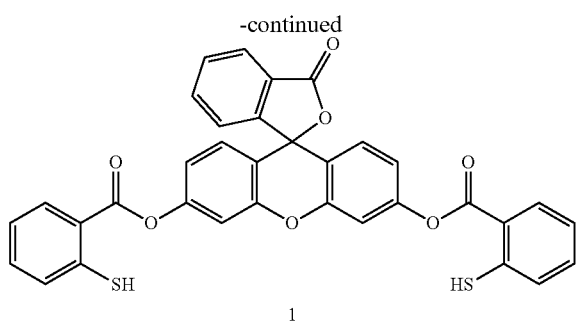

To a mixture of fluorescein (332.3 mg, 1 mmol), 2-(2-pyridinyldithio)-benzoic acid (527.1 mg, 2 mmol), EDC (384 mg, 2 mmol) and DMAP (12.2 mg, 0.1 mmol) was added CH$_2$Cl$_2$ (25 mL) at room temperature. The mixture was stirred for 10 hours. The organic layer was separated and washed with brine. After dried by anhydrous Na$_2$SO$_4$, the solvent was removed under reduced pressure and the resulted residue was used for the next step without further purification. To this intermediate (880 mg) was added THF/H$_2$O (9 mL/4 mL). Then PPh$_3$ (1.3 g, 5 mmol) was slowly added at 0° C. The mixture was allowed to warm to r.t. and stirred for 45 min. THF was removed under reduced pressure and 10 mL of HCl (1N) was added to acidify the solution. Then the mixture was extracted with ethyl acetate (40 mL). The organic layer was separated and washed with brine. After dried by anhydrous Na$_2$SO$_4$, the solvent was removed under reduced pressure and the resulted residue was purified by flash column chromatography. Compound I was obtained as a white solid (399 mg, 66% yield). $^1$H NMR (300 MHz, DMSO-d$_6$) δ 5.49 (s, 2H), 6.97 (d, J=9.0 Hz, 2H), 7.12 (d, J=9.0 Hz, 2H), 7.32 (t, J=6.0 Hz, 2H), 7.55-7.44 (m, 5H), 7.66 (d, J=9.0 Hz, 2H), 7.88-7.76 (m, 2H), 8.09 (d, J=9.0 Hz, 1H), 8.19 (d, J=6.0 Hz, 2H). $^{13}$C NMR (75 MHz, CD$_3$Cl) δ 81.9, 110.9, 116.9, 118.2, 124.3, 124.7, 125.2, 125.5, 129.3, 131.4, 132.5, 133.7, 140.1, 151.8, 152.2, 153.2, 164.9, 169.4; HRMS m/z 605.0745 [M+H]+; calcd for C$_{34}$H$_{21}$O$_7$S$_2$: 605.0729.

Synthesis of PSP Probes

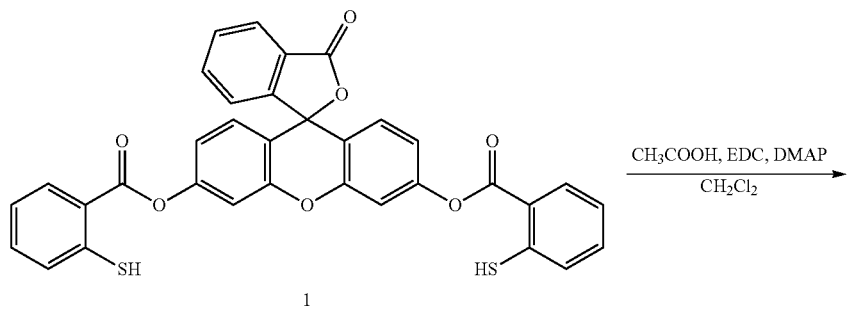

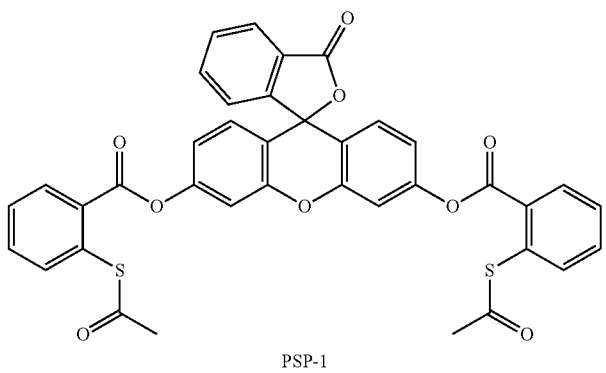

PSP-1

Probe PSP-1: To a mixture of compound 1 (121 mg, 0.2 mmol), acetic acid (30 mg, 0.5 mmol), EDC (96 mg, 0.5 mmol) and DMAP (12.2 mg, 0.1 mmol) was added CH$_2$Cl$_1$ (10 mL) at room temperature. The mixture was stirred for 3 hours. Then solvent was evaporated under reduced pressure and resulted residue was subjected to flash column chromatography for purification. PSP-1 was obtained as white solid in 96% yield. $^1$H NMR (300 MHz, DMSO-d$_6$) δ 8.20-8.17 (m, 2H), 8.09 (d, J=9.0 Hz, 1H), 7.88-7.64 (m, 8H), 7.47-7.45 (m, 3H), 7.10 (d, J=3.0 Hz, 1H), 7.07 (d, J=3.0 Hz, 1H), 7.01 (s, 1H), 6.98 (s, 1H), 2.44 (s, 6H); $^{13}$C NMR (75 MHz, CDCl$_3$) δ 193.1, 169.4, 164.3, 153.2, 152.3, 151.9, 136.9, 135.6, 133.1, 132.9, 131.8, 130.4, 129.8, 129.6, 129.3, 126.3, 125.5, 124.3, 118.1, 116.9, 110.8, 81.9, 30.6; HRMS m/z 689.0932 [M+H]+; calcd for C$_{38}$H$_{25}$O$_9$S$_2$: 689.0940.

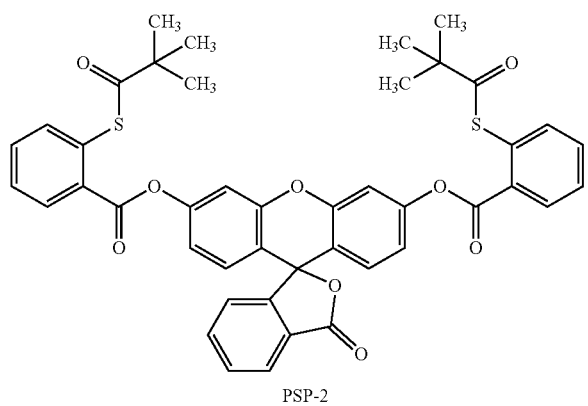

PSP-2

Probe PSP-2: To a mixture of compound 1 (121 mg, 0.2 mmol), 2,2-dimethyl propanoic acid (51 mg, 0.5 mmol), EDC (96 mg, 0.5 mmol) and DMAP (12.2 mg, 0.1 mmol) was added CH$_2$Cl$_2$ (10 mL) at room temperature. The mixture was stirred for 3 hours. Then solvent was evaporated under reduced pressure and resulted residue was subjected to flash column chromatography for purification. PSP-2 was obtained as white solid in 70% yield. $^1$H NMR (300 MHz, DMSO-d6) δ 8.19-8.16 (m, 2H), 8.08 (d, J=9.0 Hz, 1H), 7.85-7.59 (m, 8H), 7.47-7.40 (m, 3H), 7.08-6.99 (m, 4H), 1.22 (s, 18H); $^{13}$C NMR (75 MHz, CDCl$_3$) δ 203.9, 169.4, 164.5, 153.2, 152.4, 151.9, 137.3, 135.6, 133.8, 132.7, 131.6, 130.3, 129.7, 129.5, 129.3, 126.4, 125.5, 124.4, 118.1, 116.8, 110.8, 81.9, 47.2, 27.6; HRMS m/z 773.1871 [M+H]+; calcd for C$_{44}$H$_{37}$O$_9$S$_2$: 773.1879.

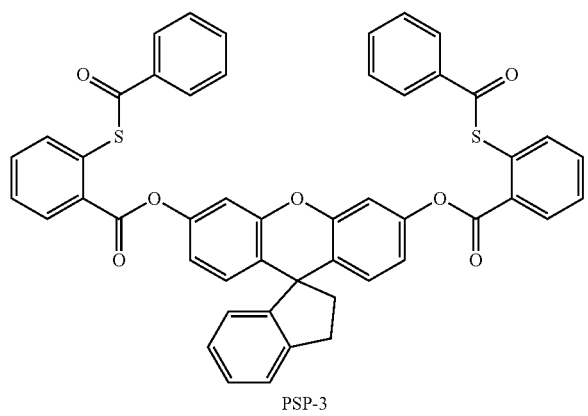

PSP-3

Probe PSP-3: To a mixture of compound 1 (121 mg, 0.2 mmol), benzoic acid (61 mg, 0.5 mmol), EDC (96 mg, 0.5 mmol) and DMAP (12.2 mg, 0.1 mmol) was added CH$_2$Cl$_2$ (10 mL) at room temperature. The mixture was stirred for 3 hours. Then solvent was evaporated under reduced pressure and resulted residue was subjected to flash column chromatography for purification. PSP-3 was obtained as white solid in 96% yield. $^1$H NMR (300 MHz, DMSO-d$_6$) δ 8.26 (d, J=6.0 Hz, 2H), 8.06-7.97 (m, 5H), 7.78-7.70 (m, 10H), 7.61-7.56 (m, 4H), 7.4-7.37 (m, 3H), 7.03 (d, J=9.0 Hz, 2H), 6.92 (d, J=9.0 Hz, 2H); $^{13}$C NMR (75 MHz, CDCl$_3$) δ 189.5, 169.4, 164.4, 153.2, 152.3, 151.8, 137.5, 136.6, 135.5, 134.1, 133.7, 133.0, 131.9, 130.2, 129.9, 129.3, 129.2, 129.1, 127.8, 126.2, 125.4, 124.3, 118.1, 116.8, 110.8, 81.9; HRMS m/z 813.1261 [M+H]+; calcd for C$_{48}$H$_{29}$O$_9$S$_2$: 813.1253.

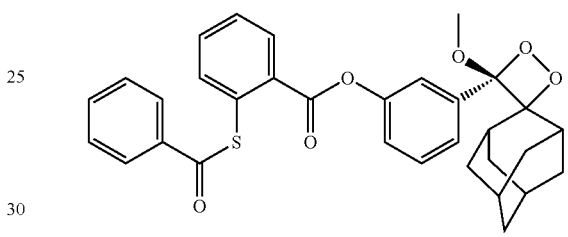

Probe PSP-5: is a chemiluminescent probe that is prepared using similar protocols for the above reference probes. 1H NMR (600 MHz, Chloroform-d) δ 8.24 (dd, J=7.7, 1.6 Hz, 1H), 8.07-8.01 (m, 2H), 7.71 (dd, J=7.6, 1.5 Hz, 1H), 7.68-7.62 (m, 1H), 7.62-7.58 (m, 2H), 7.51-7.42 (m, 3H), 7.26-7.21 (m, 2H), 3.16 (s, 2H), 3.01 (s, 1H), 2.13 (bs, 1H), 1.85 (d, J=13.1, 1H), 1.81-1.73 (m, 4H), 1.71-1.67 (m, 1H), 1.63-1.51 (m, 5H), 1.44 (dq, J=12.6, 2.7 Hz, 1H), 1.27-1.19 (m, 2H), 1.00 (d, J=13.5 Hz, 1H). 13C NMR (101 MHz, CDCl3) δ 189.21, 164.64, 137.04, 136.42, 133.95, 133.75, 132.47, 131.39, 129.58, 128.75, 128.69, 127.56, 122.72, 111.53, 95.39, 49.96, 36.35, 34.73, 33.08, 32.82, 32.26, 31.66, 31.53, 26.01, 25.79. [M+K]+C32H30O6SK=581, found: 581.

Synthesis of DPP Probes

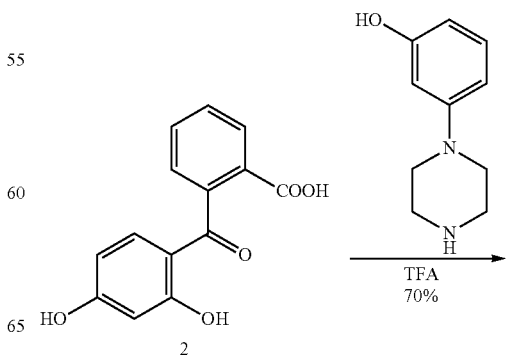

-continued

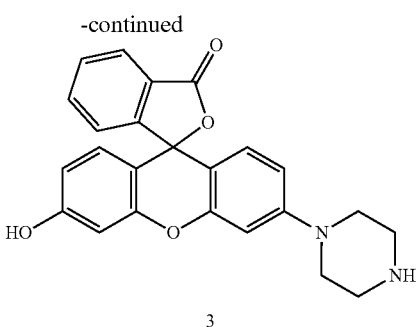

3

To compound 2 (1.42 g, 5.5 mmol) in 20 mL of TFA was added 1-(3-hydroxyphenyl)-piperazine (0.85 g, 4.8 mmol). The mixture was then heated to reflux and stirred for 36 h. After cooling, the reaction mixture was poured into 300 mL of ether. The resulting precipitate was collected and further purified by flash column chromatography. Compound 3 was obtained as a red solid (Yield: 71%). $^1$H NMR (300 MHz, DMSO-$d_6$) δ 7.99 (d, J=6.0 Hz, 1H), 7.83-7.67 (m, 2H), 7.26 (d, J=9.0 Hz, 1H), 6.78-6.65 (m, 3H), 6.66-6.49 (m, 3H), 3.17-3.09 (m, 4H), 2.85-2.78 (m, 4H).

To a mixture of Rhodol-(0.1 mmol), 2-(benzoylthio)benzoic acid (0.2 mmol), EDC (0.2 mmol) and DMAP (0.01 mmol) was added CH2Cl2 (20 mL) at room temperature. The mixture was stirred for 3 hours. Then solvent was evaporated under reduced pressure and resulted residue was subjected to flash column chromatography for purification. PSP-Rhodol was obtained as white solid in 70% yield. 1H NMR (300 MHz, DMSO-d6) δ 8.27-8.23 (m, 1H), 8.04-7.96 (m, 3H), 7.83-7.70 (m, 6H), 7.63-7.56 (m, 2H), 7.32-7.28 (m, 2H), 6.98 (dd, J=3.0, 9.0 Hz, 1H), 6.87-6.76 (m, 3H), 6.59 (d, J=9.0 Hz, 1H), 3.42-3.46 (m, 4H), 3.20-3.24 (m, 4H), 1.41 (s, 9H); 13C NMR (75 MHz, CDCl3) δ 189.3, 169.5, 164.3, 154.7, 153.1, 152.9, 152.3, 152.1, 151.9, 137.3, 136.5, 135.1, 133.9, 133.6, 132.9, 131.7, 129.9, 129.8, 129.2, 129.0, 128.9, 128.8, 127.7, 126.7, 125.1, 124.1, 117.4, 117.1, 112.4, 110.5, 109.2, 102.4, 82.8, 80.2, 48.2, 43.4, 28.5; HRMS m/z 741.2278 [M+H]+; calcd for C43H37N2O8S: 741.2271.

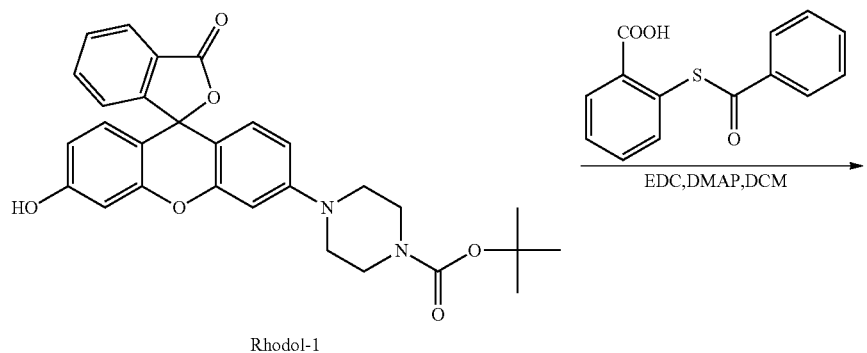

Rhodol-1

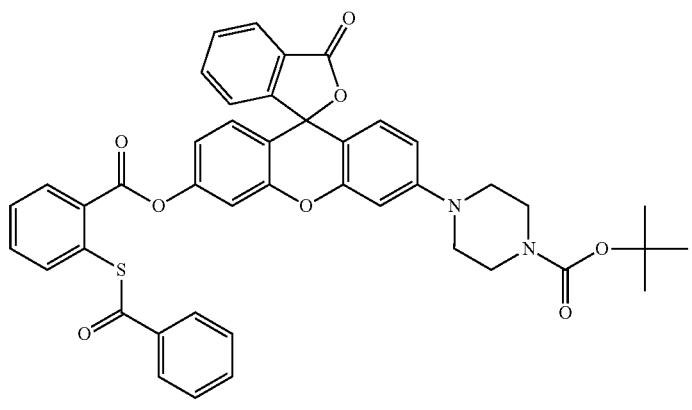

PSP-Rhodol

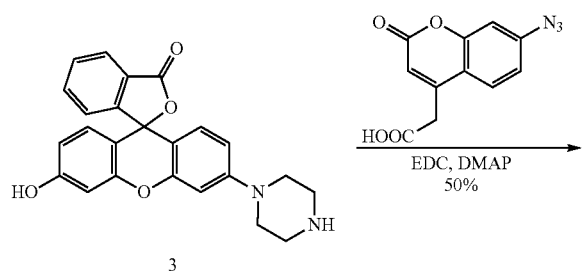

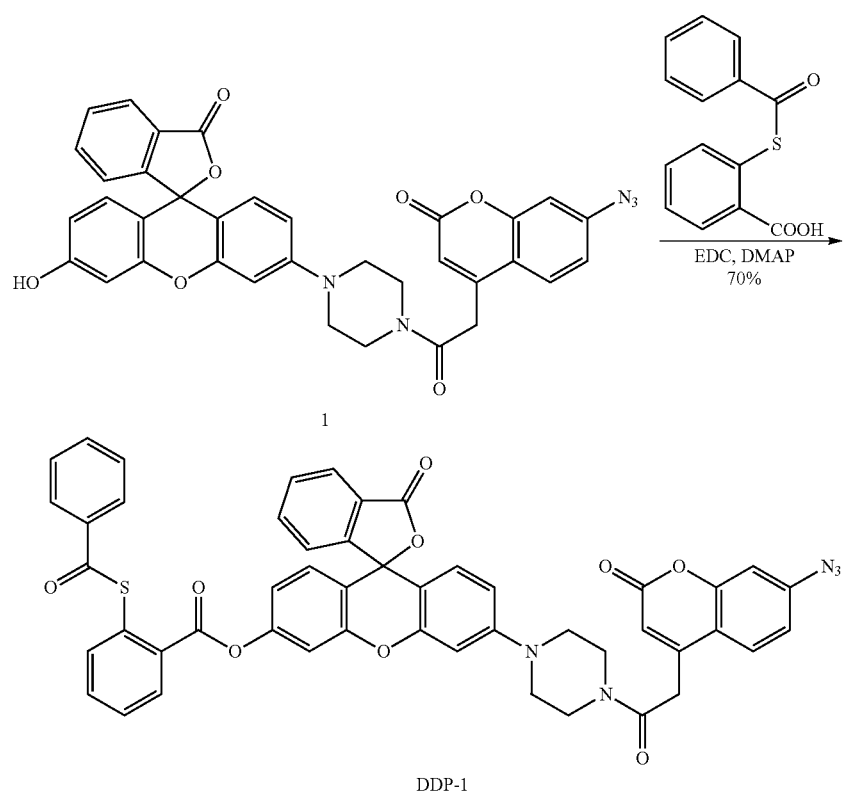

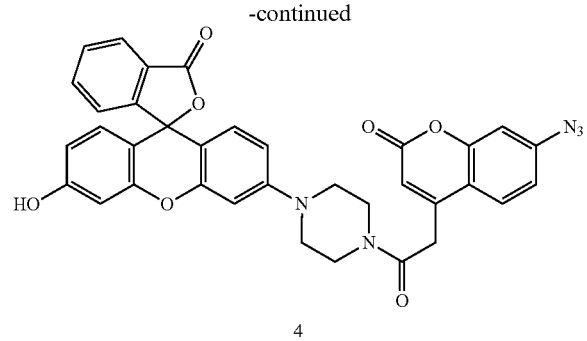

To a mixture of 7-azido-4-carbamoylmethylcoumarin (49 mg, 0.2 mmol), compound 3 (0.2 mmol), EDC (38 mg, 0.2 mmol) and DMAP (2.44 mg, 0.02 mmol) was added CH$_2$Cl$_2$/DMF (v:v 5:1, 15 mL) at room temperature. The mixture was stirred for 24 hours. Then solvent was evaporated under reduced pressure and resulted residue was subjected to flash column chromatography for purification. Compound 4 was obtained as a red solid in 50% yield. $^1$H NMR (300 MHz, DMSO-d$_6$) δ 10.15 (br, 1H), 7.99 (d, J=9.0 Hz, 1H), 7.82-7.66 (m, 3H), 7.27-7.11 (m, 3H), 6.85 (s, 1H), 6.78 (d, J=9.0 Hz, 1H), 6.67 (s, 1H), 6.58-6.52 (m, 3H), 6.35 (s, 1H), 4.09 (s, 2H), 3.72 (br, 2H), 3.60 (br, 2H), 3.39 (br, 2H), 3.27 (br, 2H); $^{13}$C NMR (75 MHz, Acetone-d$_6$) δ 169.6, 167.5, 160.3, 160.2, 155.6, 153.9, 153.5, 153.4, 153.2, 151.6, 144.4, 136.0, 130.7, 130.1, 129.5, 128.2, 127.9, 125.3, 124.9, 117.7, 116.0, 115.9, 113.2, 112.9, 111.6, 110.4, 107.5, 103.3, 102.6, 83.9, 48.9, 48.5, 46.1, 42.1, 37.3; HRMS m/z 628.1823 [M+H]+; calcd for C$_{35}$H$_{26}$N$_5$O$_7$: 628.1832.

DDP-1 Probe: To a mixture of compound 1 (62.7 mg, 0.1 mmol), 2-(benzoylthio)benzoic acid (39 mg, 0.15 mmol), EDC (29 mg, 0.15 mmol) and DMAP (6.1 mg, 0.05 mmol) was added CH$_2$Cl$_2$ (10 mL) at room temperature. The mixture was stirred for 5 hours. Then solvent was evaporated under reduced pressure and resulted residue was subjected to flash column chromatography for purification. DDP-1 was obtained as white solid in 70% yield. $^1$H NMR (300 MHz, DMSO-d$_6$) δ 8.26 (d, J=6.6 Hz, 1H), 8.04-7.97 (m, 3H), 7.79-7.57 (m, 9H), 7.32-7.29 (m, 2H), 7.19 (d, J=1.8 Hz, 1H), 7.11 (dd, J=1.8, 2.1 Hz, 1H), 6.98 (dd, J=2.1, 2.1 Hz, 1H), 6.88-6.79 (m, 3H), 6.61 (d, J=8.7 Hz, 1H), 6.34 (s, 1H), 4.09 (s, 2H), 3.72 (br, 2H), 3.60 (br, 2H), 3.39 (br, 2H), 3.29 (br, 2H); $^{13}$C NMR (75 MHz, CDCl$_3$) δ 189.3, 169.4, 166.4, 164.3, 160.1, 154.8, 152.9, 152.3, 152.2, 152.0, 151.9, 149.2, 144.1, 137.4, 136.4, 135.3, 134.0, 133.4, 132.9, 131.7, 130.0, 129.8, 129.2, 129, 128.9, 127.6, 126.6, 126.4, 125.2, 124.1, 117.6, 117.0, 116.3, 115.6, 115.3, 112.4, 110.6, 109.6, 107.3, 102.5, 82.7, 48.3, 48.1, 45.7, 41.6, 37.2; HRMS m/z 868.2067 [M+H]+; calcd for $C_{49}H_{34}N_5O_9S$: 868.2077.

Reaction of PSP Probes with $H_2S_n$

To the solution of the probe (0.02 mmol) in $CH_3CN$ (4.0 mL) and PBS buffer (4.0 mL, 50 mM, pH 7.4, containing 0.01 mmol CTAB) was added $Na_2S_2$ (0.2 mmol). The mixture was stirred for 1 h at r.t. and then diluted with ethyl acetate (50 mL). The organic layer was separated and dried by $MgSO_4$, and concentrated. Purification by flash column chromatography with hexane/ethyl acetate (3:1, v/v) afforded benzodithiolone and fluorescein as the isolated products with good yields (80%~90%).

Preparation of Solutions and Fluorescence Measurements

The stock solutions of PSP 1-3 or DDP-1 (1 mM) were prepared in DMSO, respectively. The solutions of various testing species were prepared from cysteine (Cys), GSH, homocysteine (Hcy), glutathione disulfide (GSSG), $Na_2S.9H_2O$, $Na_2S_2O_3$, $Na_2SO_3$, $Na_2SO_4$, $Na_2S_2$, $Na_2S_4$ in 50 mM PBS buffer. The stock solution of cetrimonium bromide (CTAB, 5 mM) was prepared in EtOH. The stock solution of $CH_3SSSCH_3$ (10 mM) was prepared in $CH_3CN$. The stock solution of $S_8$ (200 mM) was prepared in $CH_2Cl_2$, and then used EtOH to dilute this solution, to get 10 mM the stock solution of $S_8$ in EtOH. All of the test solution needs to be freshly prepared.

Unless otherwise noted, all the measurements were carried out for 30 min at room temperature in 50 mM PBS buffer (pH 7.4) with 100 μM CTAB according to the following procedure. In a test tube, 3 mL of 50 mM PBS buffer (pH 7.4) and 80 μL of the stock solution of CTAB were mixed, followed by the addition of a requisite volume of testing species sample solution. The final volume of the reaction solution was adjusted to 3.96 mL with 50 mM PBS buffer (pH 7.4). Then 40 μL of the stock solution of PSP 1-3 or DDP-1 (10 μM) was added. After mixing and then standing for 30 min at room temperature, a 3.5-mL portion of the reaction solution was transferred into a 1-cm quartz cell to measure fluorescence with $\lambda_{ex}$=490 nm. In the meantime, a blank solution containing no testing species sample was prepared and measured under the same conditions for comparison.

Preparation of ROS Solutions

The concentration of $H_2O_2$ was determined using the absorption at 240 nm ($\varepsilon$=43.6 $M^{-1}$ $cm^{-1}$). The concentration of $ClO^-$ was determined using the absorption at 292 nm ($\varepsilon$=360 $M^{-1}$ $cm^{-1}$). Superoxide solution ($O_2^-$) was prepared by adding $KO_2$ (1 mg) to dry dimethyl sulfoxide (1 mL) and stirring vigorously for 10 min. Hydroxy radical (.OH) was generated in situ by addition of $FeSO_4$ stock solution into a solution containing excess $H_2O_2$ through Fenton chemistry. Final concentration of $H_2O_2$ was 200 μM. Final concentration of ferrous ion was 50 μM. Singlet oxygen ($IO_2$) was generated in situ by addition of the hypochlorite stock solution into a solution containing excess of $H_2O_2$. Final concentration of $H_2O_2$ was 200 μM. Final concentration of $ClO^-$ was 50 μM.

Quantum Yields

The quantum yield of the compounds in PBS buffer was calculated according to the equation:

$$\Phi_{sample}=\Phi_{standard}\times(I_{sample}/I_{standard})\times(A_{standard}/A_{sample})\times(n_{sample}/n_{standard})^2$$

wherein, Φ denotes the quantum yield; I denotes the area under the fluorescence band; A denotes the absorbance at the excitation wavelength; n denotes the refractive index of the solvent.

For quantum yield of PSP1-3, quantum yield was determined using fluorescein as a standard by comparing the area under the corrected emission spectrum of the test sample with that of a solution of fluorescein excited at 490 nm in 0.1 N NaOH, which has a quantum efficiency of 0.85 according to the literature (H. Sunahara, Y. Urano, H. Kojima, T. Nagano, J. Am. Chem. Soc., 2007, 129, 5597-5604.).

Cell Viability Assay

HeLa cells were cultured in DMEM high glucose medium supplemented with 10% fetal bovine serum (FBS) at 37° C. under an atmosphere of 5% $CO_2$ and 95% air. The cells were then inoculated in 96-well plates and cultured overnight. DDP-1 in FBS-free medium were administered and cultured for 6 h. The cell viability was measured by cell counter kit (CCK)-8. The absorbance at 450 nm was measured with a microplate reader. Optical density (OD) of the 9 wells in the indicated groups was used to calculate percentage of cell viability according to the formula below:

Percentage of cell viability=OD treatment group/OD control group×100%

Cell Culture and Fluorescence Imaging

The cells were grown on glass-bottom culture dishes (Corning Inc.) in DMEM supplemented with 10% (v/v) FBS, penicillin (100 U/mL) and streptomycin (100 μg/mL) at 37° C. under a humidified atmosphere containing 5% $CO_2$. Before use, the adherent cells were washed one time with FBS-free DMEM. For intracellular H2Sn imaging, the cells were incubated with 5 μM the selected probe in FBS-free DMEM at 37° C. for 25 min. After removal of excess probe and washed with PBS (pH 7.4), the cells were incubated with 30 μM $Na_2S_2$ or 30 μM $Na_2S_4$ at room temperature for 20 min in PBS buffer (pH 7.4, containing 100 μM CTAB). Cell imaging was carried out after removal of the culture solution. For images of CSE-overexpressed COS7 cells.

For the imaging of D-Cys stimulated endogenous $H_2S_n$, the cells were incubated with 5 μM PSP-3 in FBS-free DMEM at 37° C. for 25 min. After removal of excess probe and washed with PBS (pH 7.4), the cells were incubated with 30 μM or 1 mM D-Cys at 37° C. for 30 min, after removal of the culture solution and use PBS buffer (pH 7.4, containing 100 μM CTAB) to further incubate at room temperature for 20 min. Cell imaging was carried out after removal of the culture solution.

It should be emphasized that the above-described embodiments and following specific examples of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

We claim:
1. A compound of formula (I):

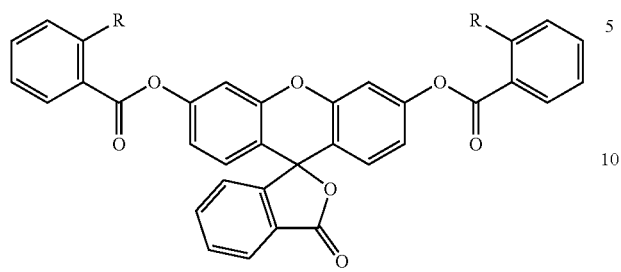

or any acceptable salt thereof, wherein
R=—SH, —OH, —SO$_2$H, —S(CO)R$_1$;
R$_1$ is selected from the group consisting of substituted alkyl, unsubstituted alkyl, substituted aryl and unsubstituted aryl.

2. The compound of claim 1, wherein R is S(CO)R$_1$ wherein R$_1$ is substituted alkyl.

3. The compound of claim 1, wherein R is S(CO)R$_1$ wherein R$_1$ is substituted aryl.

4. The compound of claim 1, and R is SH.

* * * * *